(12) United States Patent
Ariyoshi (10) Patent No.: US 11,457,796 B2
(45) Date of Patent: Oct. 4, 2022

(54) ENDOSCOPE SYSTEM AND OBJECT EVALUATION METHOD

(71) Applicant: OLYMPUS CORPORATION, Tokyo (JP)

(72) Inventor: Daiki Ariyoshi, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 383 days.

(21) Appl. No.: 16/709,193

(22) Filed: Dec. 10, 2019

(65) Prior Publication Data

US 2020/0107699 A1    Apr. 9, 2020

Related U.S. Application Data

(63) Continuation of application No. PCT/JP2018/015542, filed on Apr. 13, 2018.

(30) Foreign Application Priority Data

Jun. 13, 2017 (JP) .............................. JP2017-116234

(51) Int. Cl.
*A61B 1/00* (2006.01)
*G06T 7/00* (2017.01)
(Continued)

(52) U.S. Cl.
CPC ...... *A61B 1/00009* (2013.01); *A61B 1/00045* (2013.01); *A61B 1/0638* (2013.01);
(Continued)

(58) Field of Classification Search
CPC . G06T 7/0012; G06T 7/11; G06T 7/90; G06T 2207/10068; G06K 9/00;
(Continued)

(56) References Cited

U.S. PATENT DOCUMENTS 8,913,807 B1 * 12/2014 Horn et al. ............ G06V 10/56
382/128
2005/0165290 A1 * 7/2005 Kotsianti et al. ..... G06T 7/0012
600/407
(Continued)

FOREIGN PATENT DOCUMENTS

CN         106102554 A    11/2016
CN         106455964 A    2/2017
(Continued)

OTHER PUBLICATIONS

Machine translation of WO 2017/051779 A1 (Year: 2017).*
(Continued)

*Primary Examiner* — Andrew W Johns
(74) *Attorney, Agent, or Firm* — Scully, Scott, Murphy & Presser, P.C.

(57) ABSTRACT

An endoscope apparatus includes a display control system configured to calculate at least one index indicating a degree of abnormality of an object, according to a color included in an acquired object image, and to generate a display image in which the at least one index is identifiably displayed based on a predetermined threshold value that is set independently of the object image.

25 Claims, 9 Drawing Sheets

(51) Int. Cl.
  *A61B 1/06* (2006.01)
  *G06T 7/90* (2017.01)

(52) U.S. Cl.
  CPC .......... *A61B 1/0676* (2013.01); *G06T 7/0012* (2013.01); *G06T 7/90* (2017.01); *G06T 2207/10068* (2013.01)

(58) Field of Classification Search
  CPC ........ G06V 10/56; G06V 20/20; G06V 20/70; G06V 30/18105; A61B 1/00009; A61B 1/000094; A61B 1/00045; A61B 1/044; A61B 1/063; A61B 1/0638
  See application file for complete search history.

(56) References Cited

U.S. PATENT DOCUMENTS

| | | | |
|---|---|---|---|
| 2015/0313517 A1 | 11/2015 | Yamaguchi et al. | A61B 5/1459 |
| 2016/0379363 A1 | 12/2016 | Kitamura et al. | G06T 7/0012 |
| 2017/0049309 A1 | 2/2017 | Lepple-Wienhues | A61B 1/227 |
| 2017/0049310 A1 | 2/2017 | Lepple-Wienhues | A61B 1/227 |
| 2017/0112357 A1* | 4/2017 | Kono et al. | A61S 1/3137 |
| 2019/0269311 A1 | 9/2019 | Lepple-Wienhues | A61B 1/227 |

FOREIGN PATENT DOCUMENTS

| | | | |
|---|---|---|---|
| JP | 4632645 B2 | 2/2011 | ............... A61B 1/04 |
| JP | 2014-050594 A | 3/2014 | ............... A61B 1/00 |
| JP | 2014-094088 A | 5/2014 | ............... A61B 1/00 |
| JP | 6113943 B1 | 4/2017 | ............... A61B 1/00 |
| JP | 2018-000975 A | 1/2018 | ............... A61B 1/045 |
| WO | 2014-073358 A1 | 5/2014 | ............... A61B 1/00 |
| WO | WO 2016/009861 * | 1/2016 | ............... A61B 1/00 |
| WO | 2017/051779 A1 | 3/2017 | ............... A61B 1/00 |
| WO | 2017/078085 A1 | 5/2017 | ............... A61B 1/00 |

OTHER PUBLICATIONS

Machine translation of WO 2017/078085 A1 (Year: 2017).*
International Search Report dated Jun. 19, 2018 received in PCT/JP2018/015542.

* cited by examiner

| INDEX | IDENTIFIABLE DISPLAY INFORMATION P3 | | NORMAL /ABNORMAL |
|---|---|---|---|
| 0~9 | WHITE COLOR | | NORMAL |
| 10~19 | RED COLOR | | NORMAL |
| 20~29 | ORANGE COLOR | | NORMAL |
| 30~39 | YELLOW COLOR | | NORMAL |
| 40~49 | GREEN COLOR | | NORMAL |
| 50~59 | BLUE COLOR | | ABNORMAL |
| 60~69 | BLACK COLOR | | ABNORMAL |

FIG. 9

ENDOSCOPE SYSTEM AND OBJECT EVALUATION METHOD

CROSS REFERENCE TO RELATED APPLICATION

This application is a continuation application of PCT/JP2018/015542 filed on Apr. 13, 2018 and claims benefit of Japanese Application No. 2017-116234 filed in Japan on Jun. 13, 2017, the entire contents of which are incorporated herein by this reference.

BACKGROUND OF THE INVENTION

1. Field of the Invention

The present invention relates to an endoscope system and an object evaluation method.

2. Description of the Related Art

Conventionally, a technique has been known in which an object image is displayed after image processing is performed on the object image so that an abnormality such as inflammation of the object can be detected. For example, the description of Japanese Patent No. 4632645 discloses an imaging apparatus that generates a living body image having a scattering feature as image information, wherein, in a case where a living body tissue is modeled in two layers having a tissue surface layer and an internal layer other than the tissue surface layer, an amount of the scattering feature relating to the living body tissue is calculated by applying a mapping of one or more image values or observation values based on the image values to a scattering feature space maximizing a change in scattering feature of the tissue surface layer under a condition minimizing an influence from a change in observation values occurring due to a change in an optical characteristic of the internal layer.

In the imaging apparatus, imaging in correlation with the change in the scattering feature is performed such that a characteristic that has conventionally been difficult to observe, such as structural atypia within epithelium, can be visually recognized.

SUMMARY OF THE INVENTION

An endoscope system according to an aspect of the present invention includes a display control system configured to calculate at least one index indicating a degree of abnormality of an object, according to a color included in an acquired object image, and to generate a display image in which the at least one index is identifiably displayed based on a predetermined threshold value, wherein the at least one index is calculated by normalizing a red pixel value, a green pixel value, or a sum of the red pixel value and the green pixel value by a blue pixel value.

An object evaluation method according to another aspect of the present invention includes calculating at least one index obtained by normalizing a red pixel value or a green pixel value included in an acquired object image, or a sum of the red pixel value and the green pixel value, by a blue pixel value.

An endoscope system according to still another aspect of the present invention includes a display control system configured to calculate at least one index indicating a degree of abnormality of an object, according to a degree of yellow tinge in an acquired object image, and to generate a display image in which the at least one index is identifiably displayed based on a predetermined threshold value.

An endoscope system according to yet another aspect of the present invention includes a display control system configured to calculate at least one index indicating a degree of abnormality of an object, according to a color included in an acquired object image, and to generate a display image in which the at least one index is identifiably displayed based on a predetermined threshold value, wherein the at least one index is calculated by normalizing a green pixel value by a red pixel value.

DETAILED DESCRIPTION OF THE PREFERRED EMBODIMENT

Hereinafter, an embodiment of the present invention will be described with reference to drawings.

(Configuration)

Figure 1:
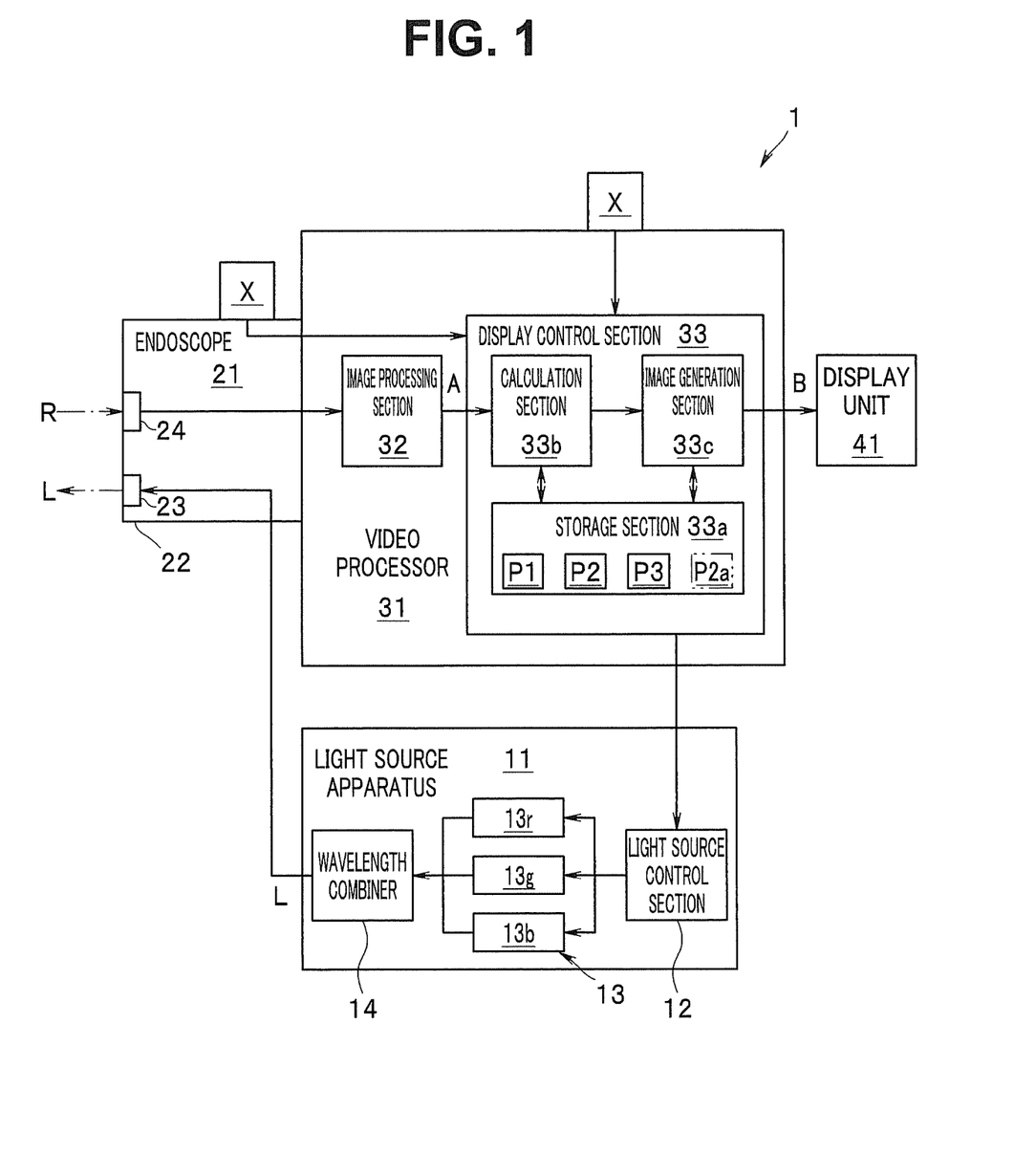
FIG. 1 is a block diagram showing an example of a configuration of an endoscope apparatus according to an embodiment of the present invention.
Figure 2:
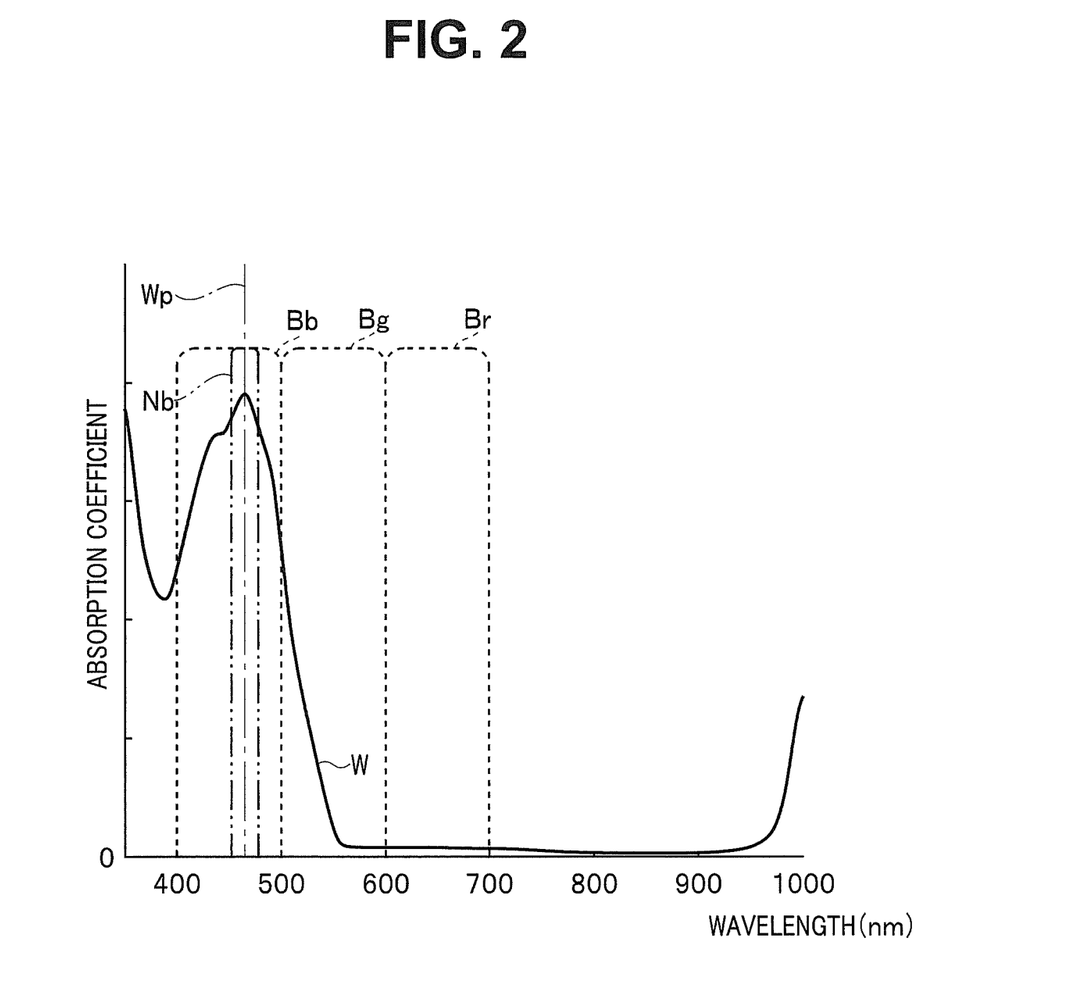
FIG. 2 is a diagram for describing a light absorption characteristic of blood plasma, according to the embodiment of the present invention.

FIG. 1 is a block diagram showing an example of a configuration of an endoscope apparatus 1 according to the embodiment of the present invention. FIG. 2 is a diagram for describing a light absorption characteristic W of blood plasma, according to the embodiment of the present invention. In FIG. 2, an X axis represents wavelengths, and a Y axis represents absorption coefficients. FIG. 2 shows ordinary-band red light Br, ordinary-band green light Bg, ordinary-band blue light Bb, narrow-band blue light Nb, the light absorption characteristic W of the blood plasma, and a wavelength Wp at which the absorption coefficient of the blood plasma peaks.

The endoscope apparatus 1 is an endoscope system including a light source apparatus 11, an endoscope 21, a video processor 31, and a display unit 41. The light source apparatus 11 is connected to each of the endoscope 21 and the video processor 31. The endoscope 21 is connected to the video processor 31. The video processor 31 is connected to the display unit 41.

The light source apparatus 11 outputs illumination light L to an illumination portion 23 that has an illumination window provided at a distal end portion of an insertion portion 22 of the endoscope 21. The light source apparatus 11 includes a light source control section 12, a light source 13, and a wavelength combiner 14.

The light source control section 12 is a circuit connected to the light source 13 and configured to control the light source 13 in accordance with the control signal inputted from a display control section 33. For example, when the control signal instructing driving of the light source apparatus 11 is inputted, the light source control section 12 instructs the light source 13 to emit light, so that the light source apparatus 11 is driven. When the control signal instructing emission of ordinary light is inputted by the display control section 33, the light source control section 12 instructs the light source 13 to output the ordinary light. When the control signal instructing emission of special light is inputted by the display control section 33, the light source control section 12 instructs the light source 13 to output the special light.

The light source 13 includes, for example, light emitting devices such as LEDs. The light source 13 includes a red light emitting portion 13r that emits red light, a green light emitting portion 13g that emits green light, and a blue light emitting portion 13b that emits blue light, and is configured to output the ordinary-band red light Br, the ordinary-band green light Bg, and the ordinary-band blue light Bb to the wavelength combiner 14 (FIG. 2).

The blue light emitting portion 13b is configured to output, in addition to the ordinary-band blue light Bb, the narrow-band blue light Nb after narrowing a band of the blue light by using, for example, a narrow-band light filter in accordance with the control signal inputted from the light source control section 12.

As shown in FIG. 2, the light absorption characteristic W of the blood plasma is low around a wavelength of 415 nm, peaks around a wavelength of 465 nm, and becomes nearly zero around a wavelength of 550 nm.

Accordingly, the band of the blue light is preferably narrowed such that a center wavelength of the light becomes equal to the wavelength Wp at which the absorption coefficient of the blood plasma peaks. For example, the band of the blue light is narrowed such that the center wavelength becomes around a wavelength of 465 nm. The band of the blue light may be narrowed such that the center wavelength falls in a range of 460 nm to 470 nm. The band of the blue light may be narrowed such that the center wavelength falls in a range of 415 nm to 495 nm.

When special light including the ordinary-band red light Br, the ordinary-band green light Bg, and the narrow-band blue light Nb is applied, the blood plasma absorbs more the blue light than the red light and the green light, and a yellow tinge more strongly appears than when the ordinary light is applied.

The wavelength combiner 14 is a device configured to combine individual colors of light inputted. The wavelength combiner 14 is connected to the illumination portion 23 and configured to combine the individual colors of the light inputted from the light source 13 and to output resultant light to the illumination portion 23.

The endoscope 21 is configured to be able to pick up an image of an inside of an object. The endoscope 21 includes the insertion portion 22, the illumination portion 23, an image pickup portion 24 that is an image pickup device, and an operation portion X.

The insertion portion 22 is formed in an elongated shape so as to be insertable into the object. Various conduits and various signal lines that are not shown are inserted in the insertion portion 22. The insertion portion 22 includes a not shown bending portion, which can be bent in according with an instruction inputted from the operation portion X.

The illumination portion 23 is provided at the distal end portion of the insertion portion 22 and configured to apply the illumination light L inputted from the light source apparatus 11 to the object.

In other words, the endoscope apparatus 1 includes the light source apparatus 11 and the illumination portion 23, wherein the light source apparatus 11 is configured to generate the special light including the ordinary-band red light Br, the ordinary-band green light Bg, and the narrow-band blue light Nb, and the illumination portion 23 is configured to apply the special light to the object.

The image pickup portion 24 is provided at the distal end portion of the insertion portion 22 and configured to acquire an object image by picking up an image of return light R from the object and to output an image pickup signal to the video processor 31. The image pickup portion 24 includes an image pickup device such as a CCD.

The operation portion X includes an instruction input device such as a button or a joystick. The operation portion X may include instruction input devices such as a touch panel, a keyboard, and a foot switch. The operation portion X is provided to each of the endoscope 21 and the video processor 31 and can receive input of various instructions to the endoscope apparatus 1. For example, the operation portion X can receive input of an instruction to bend the bending portion and an instruction to drive the light source apparatus 11, and also an instruction about a type of the illumination light L to illuminate the object and a type of an observation site of the object.

The video processor 31 is configured to control the endoscope 21, to generate an endoscope image A based on the image pickup signal inputted from the endoscope 21, and to generate a display image B based on the endoscope image A. The video processor 31 includes an image processing section 32 and the display control section 33, in addition to the operation portion X.

The image processing section 32 is a circuit configured to generate the endoscope image A by performing image processing based on the image pickup signal inputted from the image pickup portion 24. The image processing section 32 is configured to generate the endoscope image A by performing the image processing including, for example, gain adjustment, white balance adjustment, gamma correction, contour enhancement correction, and scaling adjustment based on the image pickup signal, and to output the endoscope image A to the display control section 33.

The display control section 33 is a device including a circuit configured to control each section/portion/unit in the endoscope apparatus 1. The display control section 33 as a display control system is configured by using, for example, an FPGA. The display control section 33 is connected to the display unit 41 and configured to generate the display image B based on the endoscope image A and to output the display image B to the display unit 41. The endoscope image A may be either a moving image or a still image.

The display control section 33 is configured to output the control signal to the light source apparatus 11 and to instruct the light source apparatus 11 to apply the illumination light L according to an inputted instruction to the object. More specifically, when an instruction about the ordinary light is inputted from a user through the operation portion X, the display control section 33 instructs the light source control section 12 to cause output of the ordinary light. When an instruction about the special light is inputted from the user through the operation portion X, the display control section 33 instructs the light source control section 12 to cause output of the special light.

The display control section 33 may adjust an amount of light emission from the illumination portion 23, depending on brightness of the endoscope image A.

The display control section 33 includes a storage section 33a, a calculation section 33b, and an image generation section 33c.

The storage section 33a is configured by using a storage device such as a rewritable ROM, and stores a predetermined index calculation expression P1, a predetermined threshold value P2, and identifiable display information P3.

The predetermined index calculation expression P1 is preset independently of the object image and stored in the storage section 33a. A plurality of the predetermined index calculation expressions P1 may be set according to a type of an observation mode and the type of the observation site and stored in the storage section 33a. The predetermined index calculation expression P1 is, for example, information on a calculation expression for calculating indexes.

The predetermined threshold value P2 is set so as to separate the indexes calculated by using the predetermined index calculation expression P1 into grades and stored in the storage section 33a. A plurality of the predetermined threshold values P2 may be set according to the type of the observation mode and the type of the observation site and stored in the storage section 33a.

For the identifiable display information P3, information pieces for identifiably displaying the indexes, such as colors, levels of lightness, or patterns, which are associated with ranges of the indexes separated based on the predetermined threshold value P2, are set and stored in the storage section 33a.

The calculation section 33b is a calculation device configured to calculate the indexes based on the endoscope image A. The calculation section 33b is configured to read the predetermined index calculation expression P1 from the storage section 33a, according to the type of the illumination light L and the type of the observation site inputted through the operation portion X, to calculate the indexes by using the predetermined index calculation expression P1 read, and to output the indexes to the image generation section 33c.

The image generation section 33c is a circuit configured to generate the display image B. The image generation section 33c is configured to read the predetermined threshold value P2 associated with the predetermined index calculation expression P1 and the identifiable display information P3 associated with the predetermined threshold value P2 from the storage section 33a, to determine, based on the indexes inputted from the calculation section 33b, information pieces as the identifiable display information P3 corresponding to the indexes, to generate the display image B in which the indexes are identifiably displayed, based on the information pieces as the identifiable display information P3, and to output the display image B to the display unit 41.

In other words, the display control section 33 is configured to calculate indexes indicating degrees of abnormality of the object, according to colors included in the object image acquired by the image pickup portion 24 picking up an image of the object, and to generate the display image B in which the indexes are identifiably displayed based on the predetermined threshold value P2 set independently of the object image.

The display unit 41 is configured by using, for example, a monitor capable of displaying a color image, and configured to display the display image B inputted from the image generation section 33c.

(Indexes and Predetermined Index Calculation Expression P1)

Next, the indexes and the predetermined index calculation expression P1 will be described.

FIGS. 3 to 6 are diagrams for describing the predetermined index calculation expression P1 for the endoscope apparatus 1, according to the embodiment of the present invention.

The indexes and the predetermined index calculation expression P1 are set such that the degrees of the abnormality of the object can be indicated.

Figure 3:
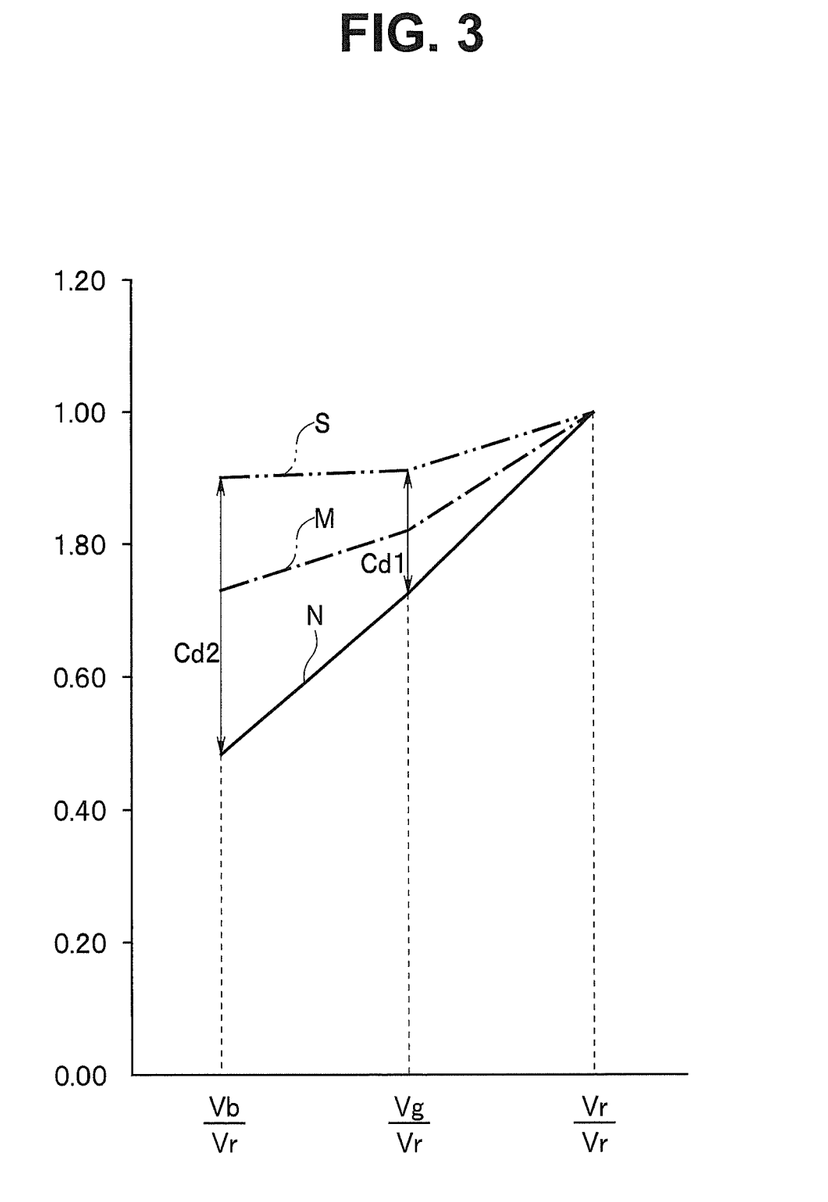
FIG. 3 is a diagram for describing a predetermined index calculation expression for the endoscope apparatus, according to the embodiment of the present invention.

In FIG. 3, each of a red pixel value Vr, which is a luminance value of a red pixel, a green pixel value Vg, which is a luminance value of a green pixel, and a blue pixel value Vb, which is a luminance value of a blue pixel, that are included in the endoscope image A acquired by picking up an image of a nose and paranasal sinuses is normalized by the red pixel value Vr. In FIG. 3, each of Vb/Vr, Vg/Vr, and Vr/Vr on the X axis represents the index calculation expression, the Y axis represents the indexes, a solid line represents normal mucosa N, a dashed dotted line represents edema M, and a dashed double dotted line represents polyp S. Hereinafter, a term "abnormal mucosa" will be used when both or any one of the edema M and the polyp S is mentioned.

Mucosa in a body, particularly mucosa in the nose and paranasal sinuses, tells a symptom that becomes severer in the order of the normal mucosa N, the edema M, and the polyp S. There is a difference in color between the normal mucosa N and the abnormal mucosa, and as a symptom becomes severer, mucosa epithelium becomes thicker, and a white tinge in appearance becomes stronger.

Regarding differences in color of the return light R between the normal mucosa N and the polyp S, as shown in FIG. 3, an index difference Cd2 for Vb/Vr on a shorter wavelength side normalized by the red pixel value Vr is greater than an index difference Cd1 for Vg/Vr on a longer wavelength side normalized by the red pixel value Vr.

In other words, the mucosa in the body has a characteristic that a greater difference in color between the normal mucosa N and the abnormal mucosa is seen on the shorter wavelength side than on the longer wavelength side. Moreover, the mucosa in the body has a characteristic that an amount of the return light R increases as the mucosa epithelium becomes thicker.

Figure 4:
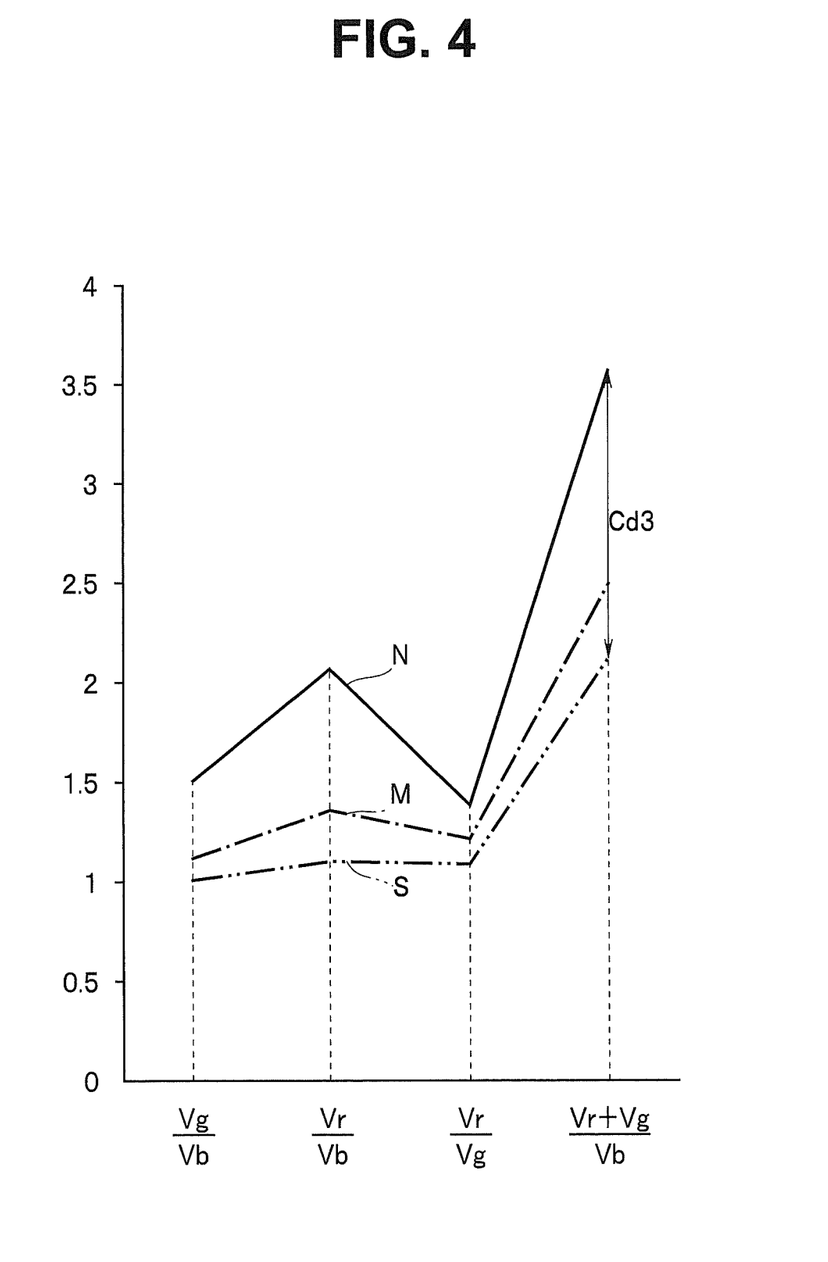
FIG. 4 is a diagram for describing the predetermined index calculation expression for the endoscope apparatus, according to the embodiment of the present invention.

FIG. 4 shows differences in result of index calculation using the index calculation expressions among the normal mucosa N, the edema M, and the polyp S. In FIG. 4, each of Vg/Vb, Vr/Vb, Vr/Vg, and (Vr+Vg)/Vb on the X axis represents the index calculation expression, and the Y axis represents the indexes.

Figure 5:
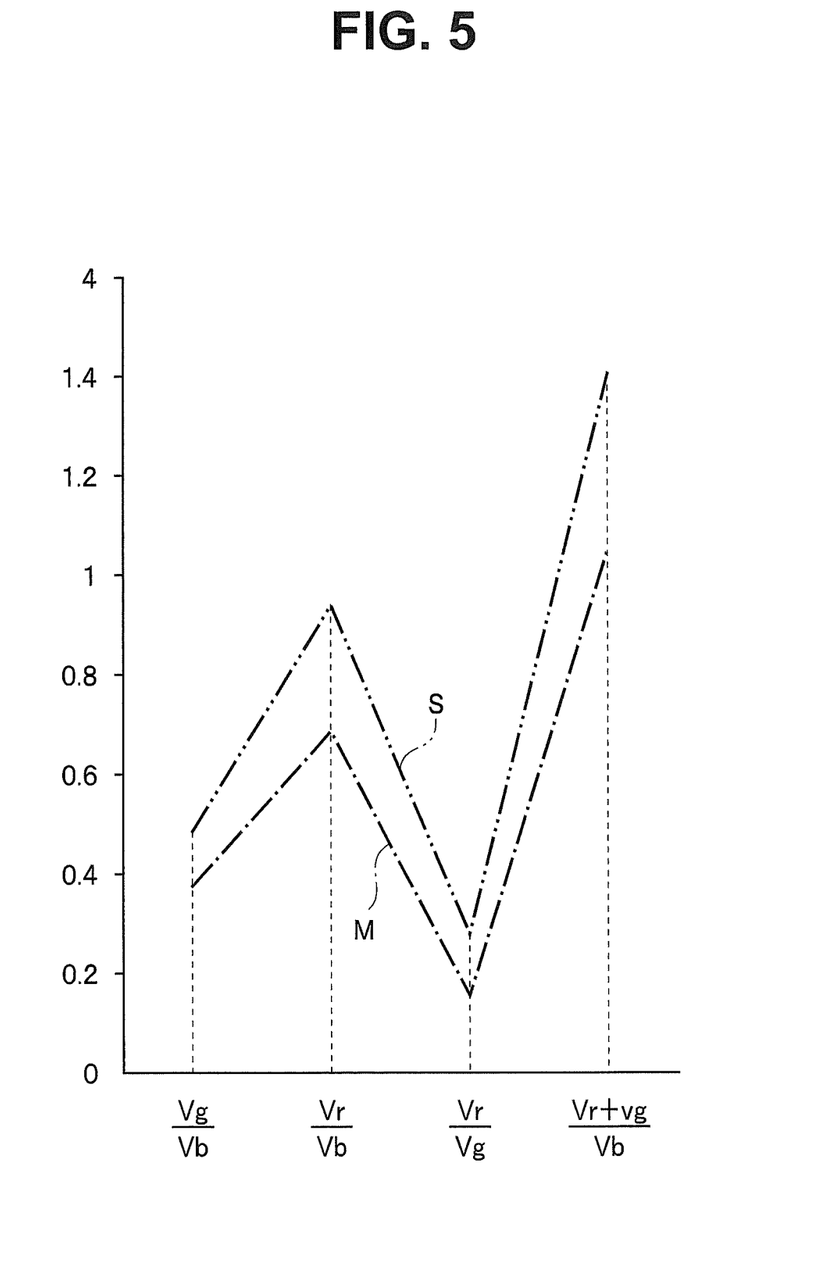
FIG. 5 is a diagram for describing the predetermined index calculation expression for the endoscope apparatus, according to the embodiment of the present invention.

FIG. 5 shows differences between the indexes of the edema M and the polyp S obtained by normalizing the edema M and the polyp S in FIG. 4 by the normal mucosa N. In FIG. 5, the X axis represents the index calculation expressions, and the Y axis represents the indexes.

As shown in FIGS. 4 and 5, regarding the normal mucosa N and the polyp S, a difference Cd3 between the indexes calculated using the index calculation expression (Vr+Vg)/Vb is greater than differences between the indexes calculated using the other index calculation expressions.

In other words, regarding the mucosa in the nose and paranasal sinuses, the indexes calculated using the index calculation expression (Vr+Vg)/Vb indicate a greater difference in color between the normal mucosa N and the abnormal mucosa.

Figure 6:
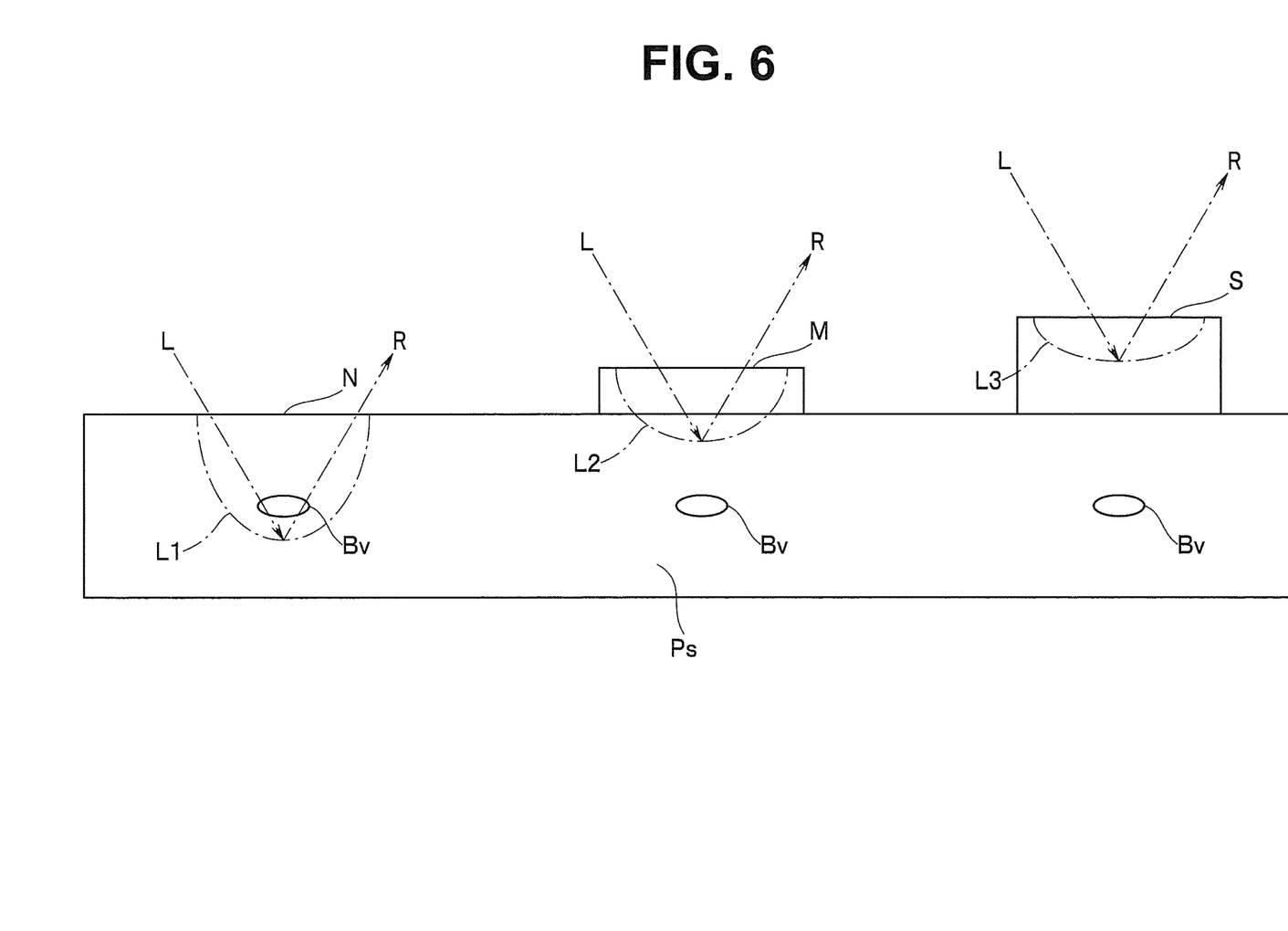
FIG. 6 is a diagram for describing the predetermined index calculation expression for the endoscope apparatus, according to the embodiment of the present invention.

FIG. 6 schematically shows a cross section of the mucosa. In FIG. 6, the normal mucosa N, the edema M, the polyp S, blood vessels By, and the illumination light L are shown. For the purpose of description, the illumination light L here is a short-wavelength light such as the blue light, and long-wavelength lights such as the red light and the green light are omitted.

As shown at a light penetration area L1 in FIG. 6, a penetration depth of the illumination light L is greater in the normal mucosa N, and it is thought that the return light R is seen as pale yellow due to pigments in the mucosa that have a higher absorption coefficient on the shorter wavelength side than on the longer wavelength side.

As shown at a light penetration area L2 in FIG. 6, it is thought that the penetration depth of the illumination light L decreases in the edema M. More specifically, in the edema M, the illumination light L is more widely scattered on the shorter wavelength side than on the longer wavelength side by hypertrophied epithelium, and returns to the image pickup portion 24 without being absorbed by the pigments in the mucosa. Accordingly, the return light R is seen as having a stronger white tinge than in the normal mucosa N.

As shown at a light penetration area L3 in FIG. 6, in the polyp S, it is thought that the light penetration depth more decreases than in the edema M, and a further stronger white tinge is seen than in the edema M.

The pigments in the mucosa are thought to be the blood plasma.

In other words, the indexes are calculated according to colors included in the object image, by using the predetermined index calculation expression P1 according to the type of the illumination light L and the type of the observation site.

The predetermined index calculation expression P1 includes the index calculation expression (Vr+Vg)/Vb obtained by normalizing a sum of the red pixel value Vr and the green pixel value Vg by the blue pixel value Vb. The index calculation expression (Vr+Vg)/Vb is preferably used for the mucosa in the nose and paranasal sinuses. Although the index calculation expression (Vr+Vg)/Vb may be used by the illumination light L that is either the ordinary light or the special light, the index calculation expression (Vr+Vg)/Vb is preferably used by the special light.

The predetermined index calculation expression P1 includes the index calculation expression Vr/Vg obtained by normalizing the red pixel value Vr by the green pixel value Vg. The index calculation expression Vr/Vg is preferably used for mucosa in digestive tract.

The predetermined index calculation expression P1 includes the index calculation expression Vr/Vb obtained by normalizing the red pixel value Vr by the blue pixel value Vb.

The predetermined index calculation expression P1 includes the index calculation expression Vg/Vb obtained by normalizing the green pixel value Vg by the blue pixel value Vb.

Note that the predetermined index calculation expression P1 may include any of expressions obtained by inverting a denominator and a numerator of each of the index calculation expression (Vr+Vg)/Vb, the index calculation expression Vr/Vg, the index calculation expression Vr/Vb, and the index calculation expression Vg/Vb. In other words, the predetermined index calculation expression P1 may include any of an expression obtained by normalizing the blue pixel value Vb by the sum of the red pixel value Vr and the green pixel value Vg, an expression obtained by normalizing the green pixel value Vg by the red pixel value Vr, and an expression obtained by normalizing the blue pixel value Vb by the red pixel value Vr or the green pixel value Vg.

(Operation)

Operation of the endoscope apparatus 1 in the embodiment will be described.

Figure 7:
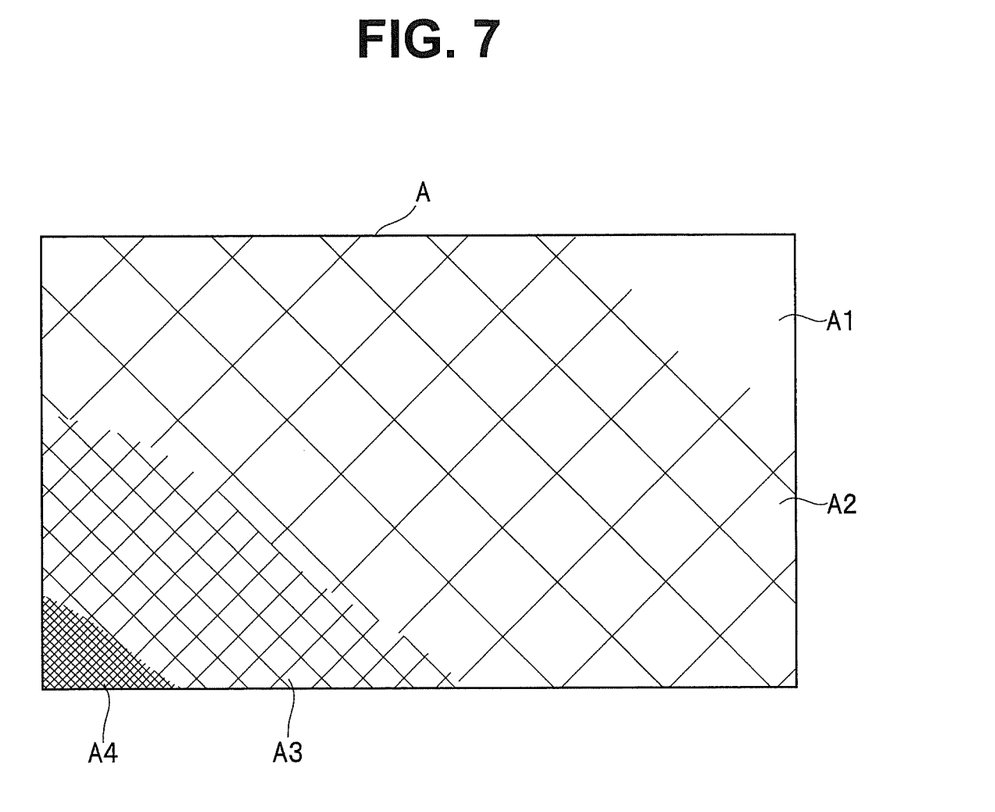
FIG. 7 is a diagram for describing an example of an endoscope image acquired by the endoscope apparatus, according to the embodiment of the present invention.
Figure 8:
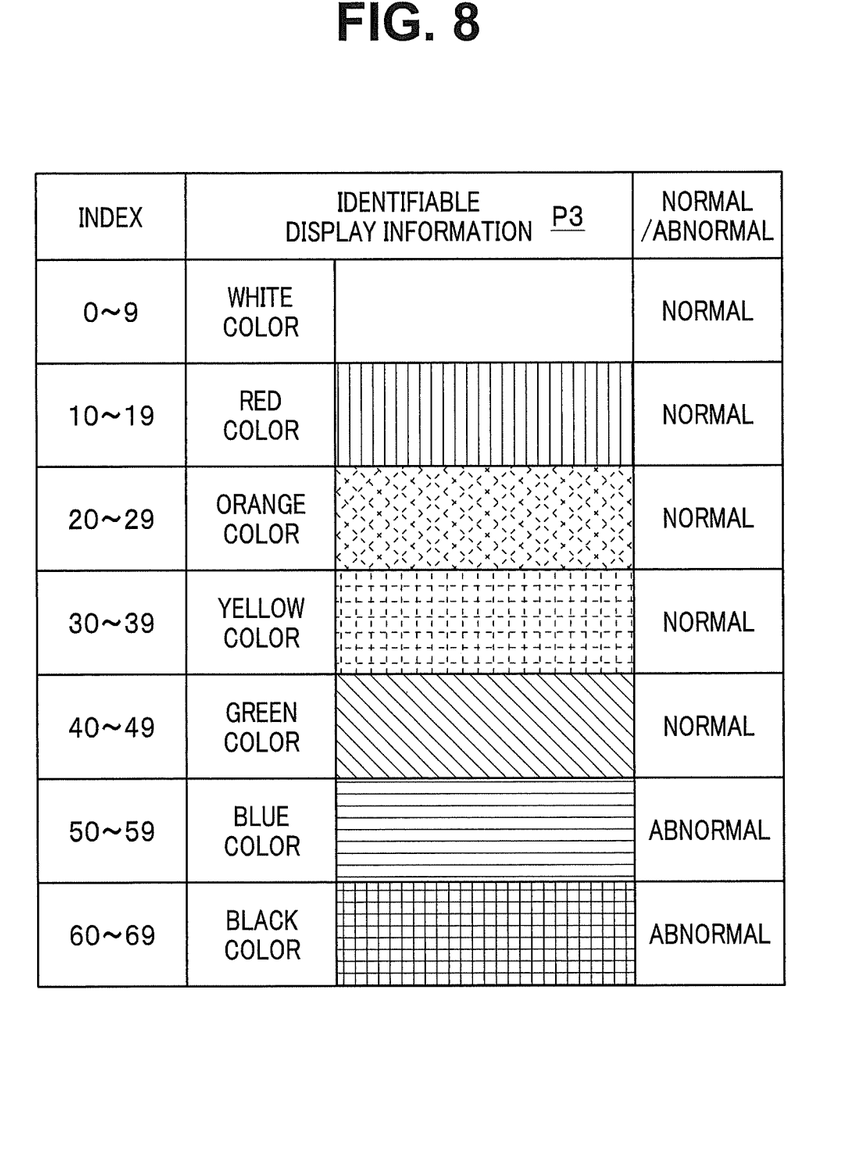
FIG. 8 is a diagram for describing an example of identifiable display information corresponding to indexes for the endoscope apparatus, according to the embodiment of the present invention.
Figure 9:
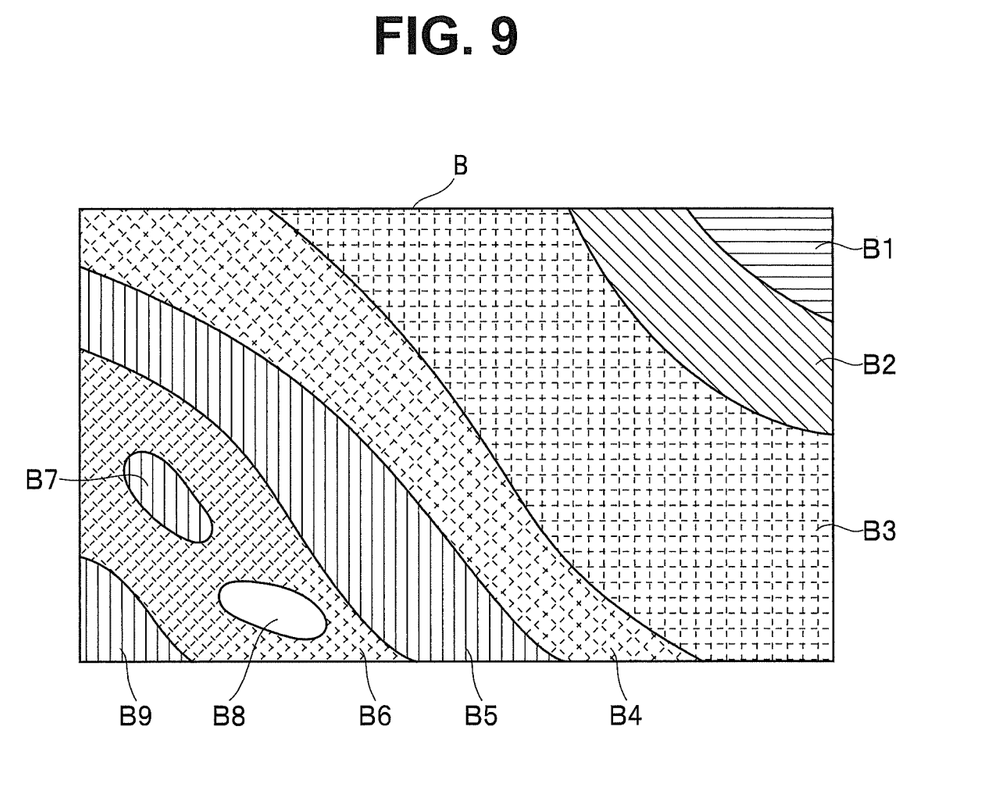
FIG. 9 is a diagram for describing an example of a display image acquired by the endoscope apparatus, according to the embodiment of the present invention.

FIG. 7 is a diagram for describing an example of the endoscope image A acquired by the endoscope apparatus 1, according to the embodiment of the present invention. FIG. 8 is a diagram for describing an example of the identifiable display information P3 corresponding to the indexes in the endoscope apparatus 1, according to embodiment of the present invention. FIG. 9 is a diagram for describing an example of the display image B acquired by the endoscope apparatus 1, according to the embodiment of the present invention.

A user inputs an instruction about, for example, the type of the observation site and the type of the illumination light L through the operation portion X. For example, the user inputs an instruction indicating that the type of the observation site is the mucosa in the nose and paranasal sinuses, and that the type of the illumination light L is the special light.

In response to the inputted instruction, the calculation section 33b reads the predetermined index calculation expression P1 from the storage section 33a.

The image generation section 33c reads the predetermined threshold value P2 associated with the predetermined index calculation expression P1 and the identifiable display information P3 associated with the predetermined threshold value P2 from the storage section 33a.

When the user inserts the insertion portion 22 into an object and inputs the instruction for applying the illumination light L to the object through the operation portion X, the display control section 33 outputs the control signal for outputting the special light to the light source control section 12. The light source control section 12 causes the red light emitting portion 13r and the green light emitting portion 13g to output the ordinary-band red light Br and the ordinary-band green light Bg, respectively, and causes the blue light emitting portion 13b to output the narrow-band blue light Nb. The wavelength combiner 14 combines the red light, the green light, and the blue light and guides the illumination light L to the illumination portion 23. The illumination portion 23 applies the illumination light L guided from the wavelength combiner 14 to the object.

The image pickup portion 24 converts the return light R from the object into the image pickup signal and outputs the image pickup signal to the image processing section 32. The image processing section 32 generates the endoscope image A based on the image pickup signal and outputs the endoscope image A to the calculation section 33b.

FIG. 7 shows an example of the endoscope image A. In the example in FIG. 7, an area A1 is white, an area A2 is pale red, an area A3 is dark red, and an area A4 is almost black. Although FIG. 7 shows the areas A1 to A4 in a simplified manner, complicated colors and patterns are seen in the actual endoscope image A.

Based on the endoscope image A, the calculation section 33b calculates the indexes by using the predetermined index calculation expression P1 read from the storage section 33a. Here, for the predetermined index calculation expression P1, (Vr+Vg)/Vb is used. The calculation section 33b decomposes the endoscope image A into RGB components, and calculates the indexes by performing an operation of (Vr+Vg)/Vb for each calculation-target pixel on the endoscope image A. The calculated indexes are outputted to the image generation section 33c.

The image generation section 33c determines the identifiable display information P3 based on the indexes inputted from the calculation section 33b and the predetermined threshold value P2.

In the example in FIG. 8, the indexes are set in a range of 0 to 69, and the predetermined threshold values P2 are set at 10, 20, 30, 40, 50, and 60. For the identifiable display information P3, the indexes of 0 to 9 are set to a white color, the indexes of 10 to 19 are set to a red color, the indexes of 20 to 29 are set to an orange color, the indexes of 30 to 39 are set to a yellow color, the indexes of 40 to 49 are set to a green color, the indexes of 50 to 59 are set to a blue color, and the indexes of 60 to 69 are set to a black color.

Note that although the plurality of colors with different hues are set for the identifiable display information P3 in the example in FIG. 8, a plurality of levels of chroma with different intensities of a color, a plurality of levels of lightness with different levels of brightness, a plurality of types of hatching with different gaps between lines, a plurality of different patterns, or the like may be set.

For example, when the value of the index is 15, the image generation section 33c determines a red color for the identifiable display information P3.

The image generation section 33c generates the display image B by placing the determined identifiable display information P3 at respective locations on the display image B corresponding to locations of the calculation-target pixels, and outputs the display image B to the display unit 41. The display unit 41 displays the display image B inputted from the image generation section 33c on the display unit 41.

The display image B generated by the image generation section 33c is color-coded according to colors indicated by the identifiable display information P3 determined based on the indexes. In the example in FIG. 9, an area B1 is blue, an area B2 is green, an area B3 is yellow, an area B4 is orange, an area B5 is red, an area B6 is orange, an area B7 is red, an area B8 is white, and an area B9 is red.

In other words, a display image generation method includes: by the image pickup portion 24, acquiring the object image by picking up an image of the object; by the calculation section 33b, calculating the indexes indicating the degrees of the abnormality of the object, according to colors included in the object image; and by the image processing section 32, generating the display image B in which the indexes are identifiably displayed based on the predetermined threshold values P2 set independently of the object image.

FIG. 8 shows the example in which of the indexes of 0 to 69, the indexes of 0 to 49 are predetermined to indicate the normal mucosa N, and the indexes of 50 to 69 are predetermined to indicate the abnormal mucosa, as diagnosis indexes. In accordance with the example, the user can quantitatively perceive that the area B1 is the abnormal mucosa and the areas B2 to B9 are the normal mucosa N.

In other words, the object is an observation-target organ; the indexes, which indicate the degrees of the abnormality of the organ according to colors of the organ, are set independently of the object image, set according to the type of the illumination light L and a type of the organ, and set such that a difference is seen between the normal mucosa N, which is a normal area of the organ, and the abnormal mucosa, which is an abnormal area of the organ; and the display image B is generated such that a difference in color between the normal area and the abnormality area is greater than a difference in color in the object image.

Thus, the user can perceive a quantitative degree of the abnormality of the object from the display image B displayed on the display unit 41.

According to the above-described embodiment, the endoscope apparatus 1 can quantitatively present the degree of the abnormality such as inflammation of the object.

Modification of the Embodiment

In the above-described embodiment, the image generation section 33c generates the display image B by placing the identifiable display information P3 at respective locations on the display image B corresponding to locations of the calculation-target pixels. However, the display image B obtained by correcting the endoscope image A according to the indexes may be generated. In the present modification, a description of the same components that are described in the embodiment is omitted.

The storage section 33a stores a predetermined threshold value P2a (dashed double dotted line in FIG. 1). The predetermined threshold value P2a is preset as a threshold value for distinguishing between the normal mucosa N and the abnormal mucosa, independently of the object image, and stored in the storage section 33a.

The image generation section 33c generates the display image B based on the indexes inputted from the calculation section 33b, the endoscope image A, and the predetermined threshold value P2a read from the storage section 33a.

More specifically, the image generation section 33c reads the predetermined threshold value P2a from the storage section 33a.

When the index inputted from the calculation section 33b is not smaller than the predetermined threshold value P2a, the image generation section 33c emphasizes a color of a pixel corresponding to the index. The color of the pixel may be emphasized by multiplying a pixel value by a predetermined coefficient k, or by adding a predetermined value to the pixel value. The color of the pixel may be emphasized by increasing the level of lightness of the pixel, or by increasing the level of chroma of the pixel.

When the index is smaller than the predetermined threshold value P2a, the image generation section 33c may be configured to make the pixel corresponding to the index unemphasized.

Thus, according to the endoscope apparatus 1, the abnormal mucosa in the endoscope image A is emphasized based on the indexes indicating the degrees of the abnormality of the object, and the degree of the abnormality of the object is quantitatively presented.

Note that although the index is calculated and identifiably displayed for the each calculation-target pixel in the endoscope image A in the embodiment and the modification, a configuration may be made such that in addition to such indexes, an overall index based on an average value of the pixel values in the entire endoscope image A is calculated and identifiably displayed. Specifically, after the average value of the pixel values in the entire endoscope image A is calculated, the overall index may be calculated based on the average value, or the overall index may be calculated by calculating the indexes for the calculation-target pixels and calculating the average value of the indexes. The calculated overall index may be identifiably displayed at a predetermined location next to the display image B, based on the predetermined threshold value P2a set for the entire endoscope image A. Thus, the endoscope apparatus 1 can quantitatively present an overall degree of inflammation in the endoscope image A. Here, identifiable display of the overall index may be made by using a plurality of colors with different hues, a plurality of types of hatching with different gaps between lines, or the like similarly to identifiable display of the respective indexes calculated for the individual calculation-target pixels, or may be made by using a numerical value representing a relationship between the overall index and the predetermined threshold value P2a or a numerical value representing the overall index itself.

Note that although the abnormality such as inflammation of the object is separated and indicated in seven degrees in the embodiment, the number of the degrees is not limited to seven. For example, the abnormality of the object may be separated and displayed in any of two to six degrees, or may be separated and displayed in eight or more degrees.

Note that although the examples in a special light observation mode are described in the embodiment and the modification, observation of the object may be performed in an ordinary light observation mode.

Note that although the examples where the observation site is the nose and paranasal sinuses are described in the embodiment and the modification, the observation site is not limited to the nose and paranasal sinuses. For example, the observation site may be another organ such as digestive tract.

Note that regardless of the predetermined index calculation expressions P1 described in the embodiment and the modification, which are given for illustrative purpose, another index calculation expression may also be included.

Note that although the functions of the display control section 33 are implemented by the FPGA in the embodiment and the modification, all or part of the functions of the display control section 33 may be implemented by a not-shown CPU and a program executed by the CPU.

Each "section/portion/unit" in the present description does not necessarily have a one-to-one correspondence with a specific hardware piece or software routine. Order in which individual procedures in the embodiment are performed may be changed, or a plurality of procedures may be performed at the same time, or the individual procedures in the embodiment may be performed in different order each time the procedures are performed, unless inconsistency occurs in the nature of the procedures. Moreover, all or part of the individual procedures in the embodiment may be implemented by using software executed by a computer.

The present invention is not limited to the above-described embodiment and modification, and various changes, modifications, and the like can be made without changing the scope of the present invention.

According to the present invention, an endoscope system and an object evaluation method that can quantitatively present a degree of abnormality such as inflammation of object can be provided.

What is claimed is:

1. An endoscope system, comprising a processor configured to calculate at least one index indicating a degree of abnormality of an object, according to a color included in an acquired object image, and to generate a display image in which the at least one index is identifiably displayed based on a predetermined threshold value,
wherein the at least one index is calculated by normalizing a red pixel value, a green pixel value, or a sum of the red pixel value and the green pixel value by a blue pixel value.

2. The endoscope system according to claim 1, further comprising an image sensor,
wherein the object image is acquired by the image sensor performing image pickup.

3. The endoscope system according to claim 1,
wherein the object is an organ, and the display image is generated such that a difference in color between a normal area and an abnormal area is greater than a difference in color in the object image.

4. The endoscope system according to claim 1,
wherein the predetermined threshold value is set so as to separate the at least one index into grades.

5. The endoscope system according to claim 1,
wherein a plurality of the predetermined threshold values are set according to a type of an observation mode and a type of an observation site.

6. The endoscope system according to claim 1, wherein the processor is configured to receive a signal of an inputted instruction about a type of illumination light that illuminates the object, and a type of an observation site of the object.

7. The endoscope system according to claim 6,
wherein the observation site is mucosa in a nose and paranasal sinuses.

8. The endoscope system according to claim 1, comprising a first light source, a second light source, a third light source and an illumination window,
wherein lights of the first light source, the second light source and the third light source are combined to obtain a special light, the first light source generating ordinary-band red light, the second light source generating ordinary-band green light the third light source generating narrow-band blue light, and
wherein the illumination window is configured to apply the special light to the object.

9. The endoscope system according to claim 8,
wherein the blue light is made to have a narrow band in which a center wavelength is equal to a wavelength at which an absorption coefficient of blood plasma peaks.

10. The endoscope system according to claim 8,
wherein the blue light is made to have a narrow band in which a center wavelength falls in a range of 415 nm to 495 nm.

11. The endoscope system according to claim 8,
wherein the blue light is made to have a narrow band in which a center wavelength falls in a range of 460 nm to 470 nm.

12. The endoscope system according to claim 1, further comprising a memory configured to store a predetermined index calculation expression, the predetermined threshold value, and identifiable display information,
wherein the processor is configured to:
read the predetermined index calculation expression from the memory, and calculate the at least one index by using the predetermined index calculation expression read; and
read the predetermined threshold value associated with the predetermined index calculation expression and the identifiable display information associated with the predetermined threshold value from the memory, to determine the identifiable display information corresponding to the at least one index, based on the at least one index, and to generate the display image in which the at least one index is identifiably displayed, based on the identifiable display information.

13. The endoscope system according to claim 1,
wherein the predetermined threshold value is set independently of the object image.

14. The endoscope system according to claim 1, wherein the processor is configured to calculate the at least one index by normalizing a sum of the red pixel value and the green pixel value by the blue pixel value.

15. The endoscope system according to claim 1, wherein the object is mucosa.

16. The endoscope system according to claim 1, wherein the index indicates a degree of system of edema or polyp as the degree of abnormality.

17. A calculation method comprising, by a calculation device, calculating at least one index indicating a degree of abnormality of an object, according to a color included in an acquired object image, wherein the at least one index is calculated by normalizing a red pixel value or a green pixel value included in an acquired object image, or a sum of the red pixel value and the green pixel value, by a blue pixel value.

18. The calculation method according to claim 17, comprising generating a display image in which the at least one index is identifiably displayed based on a predetermined threshold value.

19. The calculation method according to claim 18, wherein the predetermined threshold value is set independently of the object image.

20. The calculation method according to claim 17, wherein the object image is acquired by an image sensor picking up an image of an object.

21. An endoscope system comprising a processor configured to calculate at least one index indicating a degree of abnormality of an object, according to a degree of yellow tinge in an acquired object image, and to generate a display image in which the at least one index is identifiably displayed based on a predetermined threshold value.

22. The endoscope system according to claim 21, wherein the degree of yellow tinge is a degree of strength of light having wavelengths of 565 to 590 nm.

23. The endoscope system according to claim 21, further comprising an image sensor, wherein the object image is acquired by the image sensor performing image pickup.

24. An endoscope system comprising a processor configured to calculate at least one index indicating a degree of abnormality of an object, according to a color included in an acquired object image, and to generate a display image in which the at least one index is identifiably displayed based on a predetermined threshold value, wherein the at least one index is calculated by normalizing a green pixel value by a red pixel value.

25. The endoscope system according to claim 24, further comprising an image sensor, wherein the object image is acquired by the image sensor performing image pickup.

* * * * *